United States Patent [19]

Sakaguchi et al.

[11] Patent Number: 4,705,039
[45] Date of Patent: Nov. 10, 1987

[54] SUBSIDIARY DEVICE FOR SUTURING AN INTESTINE

[75] Inventors: Ushio Sakaguchi; Masahiro Nakano; Mitsukuni Uchida, all of Kumamoto, Japan

[73] Assignee: Takasago Medical Industry, Co., Ltd., Tokyo, Japan

[21] Appl. No.: 759,416

[22] Filed: Jul. 26, 1985

[30] Foreign Application Priority Data

Jul. 28, 1984 [JP] Japan .......................... 59-115180[U]

[51] Int. Cl.⁴ ................................................ A61B 17/04
[52] U.S. Cl. ................................ 128/334 C; 128/334 R
[58] Field of Search ............... 128/334 C, 346, 334 R, 128/335.5, 325, 335; 623/1, 11, 12, 66

[56] References Cited

U.S. PATENT DOCUMENTS

| | | | |
|---|---|---|---|
| 2,638,901 | 5/1953 | Surgarbaker | 128/334 R |
| 3,155,095 | 11/1964 | Brown | 128/334 C |
| 3,765,414 | 10/1973 | Arlen | 623/66 |
| 4,055,186 | 10/1977 | Leveen | 128/334 C |
| 4,337,774 | 7/1982 | Perlin | 128/346 |
| 4,467,804 | 8/1984 | Hardy et al. | 128/334 C |
| 4,532,134 | 7/1985 | Malette et al. | 128/334 R |

Primary Examiner—Richard C. Pinkham
Assistant Examiner—Gary Jackson
Attorney, Agent, or Firm—Kenyon & Kenyon

[57] ABSTRACT

The male tube at one end is provided with a connecting tubular piece adapted to fit into the female tube. The female tube in the connected position of the tubes is provided with a hole for inserting a pin in order to secure the connection of both tubes. The material for forming the tubes may be coated with a thin film of slowly water soluble polymeric material in order to allow a delayed dissolution of the tubes into the intestinal fluid.

5 Claims, 4 Drawing Figures

SUBSIDIARY DEVICE FOR SUTURING AN INTESTINE

FIELD OF THE INVENTION

This invention relates to a subsidiary device for suturing an intestine in anastomosis, which may be inserted into the intestine for connecting the separate intestinal ducts in a convenient anastomotic operation and may be dissolved into an intestinal fluid without necessity of recovering the same from a patient.

BACKGROUND OF THE INVENTION

When separate intestinal ducts are sutured in anastomosis, the time required for the suturing is considerable due to softness and flexibility of an intestine.

In order to achieve a convenient suturing operation, a number of attempts have been made to develop various anastomotic devices. Since any device should be operated while keeping the soft and flexible intestinal ducts in a constantly connected position, such suturing device must have both a supporting means and a suturing means, resulting in a more complicated, expensive and inconvenient device.

Accordingly, an object of the invention is to provide a subsidiary device for anastomosis, which is simple in construction and permits convenient suturing operation.

SUMMARY OF THE INVENTION

In view of the foregoing, the invention provides a subsidiary device for suturing an intestine in anastomosis, which comprises two tubes of an equal outer diameter insertable into the intestine, said tubes being formed of a solubilizable material in an intestinal fluid and being connectable to each other.

For better understanding, the invention will be described in more detail with reference to the accompanying drawings.

PREFERRED EMBODIMENTS OF THE INVENTION

Figure 1:
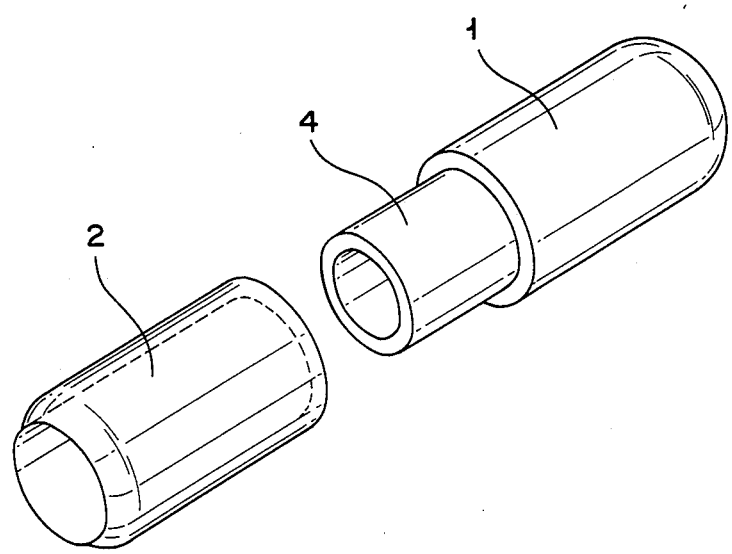
FIG. 1 is a perspective view of the device according to the invention.

In the drawings, a reference numeral 1 represents a male tube while a reference numeral 2 represents a female tube, which tubes 1, 2 have an equal outer diameter insertable into an intestine 3.

Figure 4:
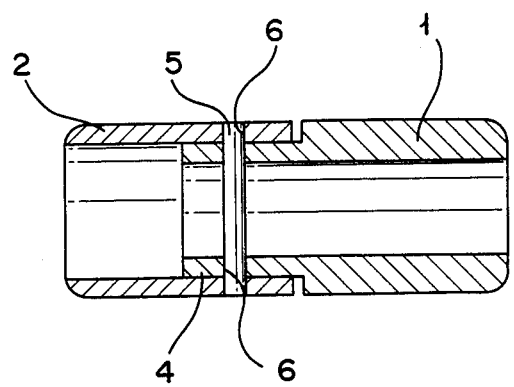
FIG. 4 is a longitudinal sectinal view of another embodiment of the device according to the invention, showing its connected position.

The male tube 1 at its one end is provided with a connecting tubular piece 4 which may be fitted into the female tube 2 in the form of a spigot joint. If desired, as shown in FIG. 4, the female tube 2 in the connected position of the tubes is provided with a hole 6 for inserting a pin 5 through the connecting piece in order to secure connection of both tubes 1 and 2.

The tubes 1, 2 are formed of a solubilizable material in an intestinal fluid through absorption of water, such as natural polymeric materials including gelatine, albumin, dextran, chitosan and pluran; cellulose derivatinves including hydroxypropylcellulose, hydroxypropylmethylcellulose, methylcellulose, carboxymethylcellulose and carboxymethylethlcellulose; and synthetic polymers including polyvinyl alcohol, polyacrylamide, polyacrylic acid, polyethylene oxide and polyvinyl pyrrolidone.

If desired, the material for forming the tubes may be coated with a thin film of a hardly or slowly water-soluble polymeric material, such as ethylcellulose and celluloseacetate, in order to allow delayed dissolution of the tubes into the intestinal fluid.

The male and female tubes 1, 2 may be formed as follows: The natural polymeric material, the cellulose derivative or the synthetic polymer is dissolved in water or an organic solvent and then poured into a mold. Then, the water or organic solvent is removed to leave a formed tube which is then dried.

As an example one part of an alkaline-treated gelatin (NITTA Gelatin #200) was swollen with 1–1.25 parts of purified water at a room temperature. Then, the material was dissolved in the aqueous solution at 60°–70° C. and stirred violently into a metal mold which had previously been heated to 60–70° C. Thereafter, the mold was cooled with ice to gelatinize the material which was then removed from the mold. The removed material had a shape of the male or female tube 1,2 depending on a type of the mold. The tube was fitted onto a Teflon rod of the same diameter and frozen for more than two hours in a freezer. Then, the perfectly frozen gelatin fitted on the rod was placed in a freeze-dryer to be dehydrated and dried for 8–30 hours. Thereafter, the perfectly dried gelatin tube was removed from the rod, immersed into a solution consisting of 5% ethylcellulose and 95% ethanol (supplied from TOKYO KASEI KOGYO CO., LTD., 45 cps.) and then dried at a room temperature to apply an ethylcellulose coating on the gelatin surface.

During the above procedure, the purpose of violently stirring the dissolved gelatin is to introduce small bubbles into the gelatin for ensuring uniform low shrinkage upon the drying procedure. The purpose of freeze-drying is to reduce the shrinkage of gelatin upon drying, while the purpose of applying the ethylcellulose coating on the gelatin surface is to prevent water from penetrating into the gelatin and thus to keep a strength of the gelatin tube for 30–60 minutes. Further, a thickness of the ethylcellulose coating may be adjusted for controlling a necessary time for softening and dissolving the gelatin tube into the intestinal fluid.

Figure 2:
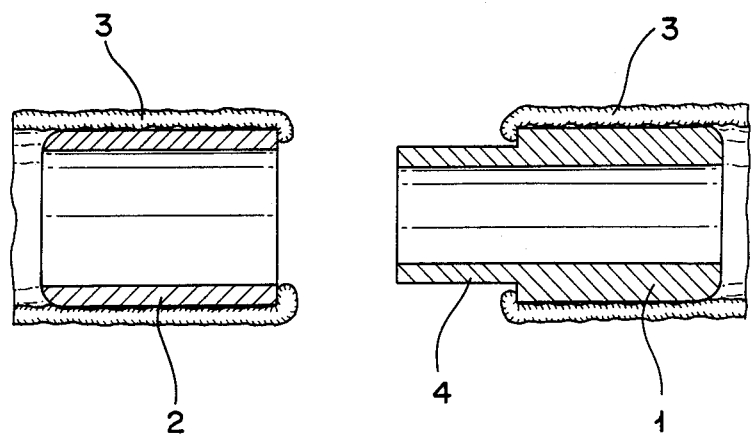
FIG. 2 is a longitudinal sectional view of the device, showing two separate tubes each inserted into severed intestine.

In the anastomotic operation, as shown in FIG. 2, one of the severed intestinine ducts 3, 3 is provided thereinto with the male tube 1 with its connecting tubular piece 4 being positioned outside the duct, while the other intestine duct 3 is provided thereinto with the female tube 2. If desired, the tubes 1, 2 on their inserted ends may be rounded or chamfered for convenient insertion.

Figure 3:
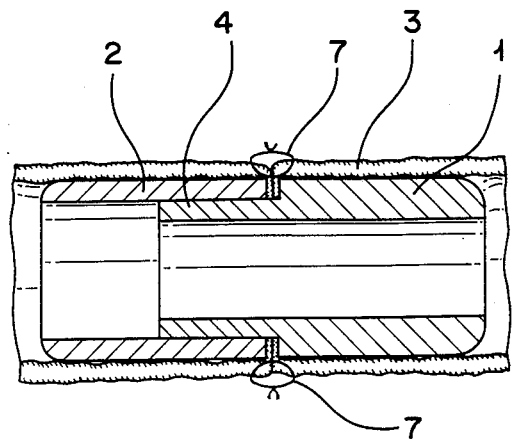
FIG. 3 is a longitudinal sectional view of the device during a suturing procedure.

After insertion of each tube 1 or 2 into the respective intestine 3, an end of the intestine is bent inwardly, as shown in FIG. 2, to slightly cover an exposed end of the tube in the form of a flange. Then, as shown in FIG. 3, the connecting piece 4 is fitted into the female tube 2 with the flanged portion of the intestine being secured between the tubes 1, 2. Then, the suturing operation may be conveniently carried out, using a suturing string 7.

Thus, notwithstanding the softness and flexibility of the intestine, the rigid male and female tubes 1, 2 may be inserted into the ducts 3, 3 for their connection, thereby to prevent the ducts to be separated from each other during the suturing procedure and thus to ensure convenient suturing operation in a short time.

After the suturing operation, the tubes 1, 2 are left in the intestine 3 but may be dissolved into the intestinal fluid subsequently and excreted as feces from a patient. As a result, unnecessity of removal of tubes from the intestine may lead to early recovery of the patient from the surgical operation.

In accordance with the invention, the subsidiary device for the anastomosis comprises two tubes 1, 2 of an equal outer diameter insertable into an intestine 3, which tubes are formed of a solubilizable material in an intestinal fluid and are connectable to each other, so that the rigid tubes may be inserted into the intestine ducts 3, 3 for their connection, thereby to prevent the ducts 3, 3 to be separated from each other during the suturing operation and thus to ensure the convenient suturing operation in a short time.

After the suturing procedure, the tubes 1, 2 are left in the intestine 3 but may be dissolved into the intestinal fluid subsequently and excreted as feces from a patient, so that the early recovery of the patient may be achieved after the surgery.

As described hereinabove, the device according to the invention is very simple in construction without need of special means and may be dissolved in the intestinal fluid, so that it may be conveniently handled and manufactured in a low cost.

What is claimed is:

1. An anastomotic device, comprising:
   a first tubular member, formed as a hollow cylinder and having a smooth exterior wall, with a projecting member extending from an end thereof, said projection being cylindrical in shape and having an outer diameter smaller than the outer diameter of said first member; and
   a second tubular member, formed as a hollow cylinder and having a smooth exterior wall, the inside diameter thereof defining a receiving portion dimensioned to accept said projection within the inside diameter of same;
   said first and second tubular members being formed of a material soluble in an intestinal fluid;
   whereby said first tubular member is inserted in one portion of an elongated object of anastomosis, said second tubular member is inserted in a second portion of said elongated object, and said first member projection is inserted into the receiving portion of said second member to stabilize said object for suturing;
   wherein the material for forming said device is selected from the group consisting of gelatin, albumin, dextran, chitosan, pluran, hydroxypropylcellulose, hydroxypropylmethylcellulose, methylcellulose, carboxymethylcellulose, carboxymethylethylcellulose, polyvinyl alcohol, polyacrylamide, polyacrylic acid, polyethylene oxide and polyvinyl pyrrolidone; and
   wherein the material is coated with a thin film of a water-soluble polymeric material selected from the group consisting of ethylcellulose and celluloseacetate.

2. The device of claim 1, wherein said soluble material for forming said device is a natural polymer.

3. The device of claim 1, wherein said soluble material for forming said device is a cellulose derivative.

4. The device of claim 1, wherein said soluble material for forming said device is a synthetic polymer.

5. A device according to claim 1, wherein said tubular members are provided with a hole for inserting a fixing pin for securing connection of the two tubes.

* * * * *

UNITED STATES PATENT AND TRADEMARK OFFICE
CERTIFICATE OF CORRECTION

PATENT NO. : 4,705,039

DATED : November 10, 1987

INVENTOR(S) : SAKAGUCHI, et al.

It is certified that error appears in the above-identified patent and that said Letters Patent is hereby corrected as shown below:

```
    Col. 1, line 35, change "solubilizable material" to
--material solubilizable--.
    Col. 1, line 66, change "solubilizable material" to
--material solubilizable--.
    Col. 1, line 49, change "sectinal" to --sectional--.
    Col. 2, line 1, change "derivatinves" to
--derivatives--.
    Col. 2, line 4, change "carboxymethylethlcellulose" to
--carboxymethylethylcellulose--.
    Col. 2, line 21, change "at a room" to --at room--.
    Col. 2, line 38, change "at a room" to --at room--.
    Col. 2, line 22, change "60°-70" to --60°-70--.
    Col. 2, line 24, change "60°-70" to --60°-70--.
    Col. 2, line 47, change "keep a" to --retain the--.
    Col. 2, line 50, change "a necessary" to
--the required--.
    Col. 2, line 53, change "intestinine" to --intestinal--.
    Col. 3, line 18, change "intestine" to --intestinal--.
    Col. 3, line 20, change "to be" to --from being--.
    Col. 3, line 32, change "in" to --at--.
```

Signed and Sealed this

Second Day of January, 1990

Attest:

JEFFREY M. SAMUELS

*Attesting Officer*  *Acting Commissioner of Patents and Trademarks*